United States Patent [19]

Kagitani et al.

[11] Patent Number: 4,560,556

[45] Date of Patent: Dec. 24, 1985

[54] FIBRONECTIN-PHYSIOLOGICALLY ACTIVE SUBSTANCE COMPLEX AND METHOD OF PREPARATION THEREOF

[75] Inventors: Yoshio Kagitani, Kashihara; Kenji Tanaka, Yamatokoriyama; Yasuo Ueda, Hirakata; Yusei Shiraga, Kobe; Tunetaka Nakajima, Kashiwara; Takuji Doi, Kyoto; Takao Ohmura, Toyonaka, all of Japan; Satoshi Funakoshi, Los Angeles, Calif.; Tadakazu Suyama, Kyoto, Japan

[73] Assignee: The Green Cross Corporation, Osaka, Japan

[21] Appl. No.: 572,750

[22] Filed: Jan. 23, 1984

[30] Foreign Application Priority Data

Jan. 21, 1983 [JP] Japan .................................. 58-8912

[51] Int. Cl.[4] ........................ C07G 7/00; A61K 35/16; A61K 37/04
[52] U.S. Cl. ................................ 424/101; 260/112 B; 514/21

[58] Field of Search ............................... 424/101, 177; 260/112 B; 514/21

[56] References Cited

U.S. PATENT DOCUMENTS

| | | | |
|---|---|---|---|
| 4,093,607 | 6/1978 | Sela et al. | 260/112 B |
| 4,210,580 | 7/1980 | Amrani | 260/112 B |
| 4,315,906 | 2/1982 | Gelder | 260/112 B X |
| 4,341,764 | 7/1982 | Wallace et al. | 260/112 B X |
| 4,376,765 | 3/1983 | Trouet et al. | 424/177 |
| 4,391,749 | 7/1983 | Engvall et al. | 260/123.7 |
| 4,440,679 | 4/1984 | Fernandes et al. | 260/112 B X |

*Primary Examiner*—Howard E. Schain
*Attorney, Agent, or Firm*—Cushman, Darby & Cushman

[57] ABSTRACT

Physiologically active substances such as antibiotics can preferentially be carried to a morbid part, for example, injured tissue and neoplastic cell proliferation site by administering its complex with fibronectin to repair the morbid part. The complex is prepared by the reaction between the physiologically active substance and the fibronectin with or without intervention of a protein cross-linking agent.

7 Claims, No Drawings

FIBRONECTIN-PHYSIOLOGICALLY ACTIVE SUBSTANCE COMPLEX AND METHOD OF PREPARATION THEREOF

BACKGROUND OF THE INVENTION

This invention relates to a novel fibronectin-physiologically active substance complex and the preparation thereof. More particularly it relates to a method of preparing a fibronectin-physiologically active substance complex resulting from combining a fibronectin, which has a high affinity for a morbid part such as an injured tissue or a neoplastic cell proliferation site with a physiologically active substance capable of protecting and repairing these tissues and sites and the thus prepared complex.

It is a common practice to administer various physiologically active substances systemically to prevent the suppuration of a wounded site, to promote the repair of an inflamed site, and to destory cancer cells. In this case it is unavoidable at present to administer a large amount of the physiologically active substance in order to attain to a sufficient concentration to exert its effect.

Especially in the case of administering an antitumor substance, since the dose giving a manifest effect and that giving a manifest side effect are frequently in close proximity, the large-amount administration is often compelled to be discontinued owing to the manifestation of the side effect even when a promising This invention relates to a novel fibronectin-physiologically active substance complex and the preparation thereof. More particularly it relates to a method of preparing a fibronectin-physiologically active substance complex resulting from combining a fibronectin which has a high affinity for a morbid part such as an injured tissue or a neoplastic cell proliferation site with a physiologically active substance capable of protecting and repairing these tissues and sites and thus prepared complex.

It is a common practice to administer various physiologically active substances systemically to prevent the suppuration of wounded site, to promote the repair of inflamed site, and to destroy the cancer cells. In this case it is unavoidable at present to administer a large amount of the physiologically active substance in order to attain to a sufficient concentration to exert its effect.

Especially in the case of administering an antitumor substance, since the dose gving a manifest effect and that giving a manifest side effect are frequently in close proximity, the large-amount administration is often compelled to be discontinued owing to the manifestation of the side effect even when a promising effect can be expected, leading thus to a fatal result. In order to avoid such situations, it is necessary to accumulate the physiologically active substance specifically in the morbid part as an injured tissue such as a wounded site and an inflamed site, or a neoplastic cell proliferation site.

The inventors have made intensive studies based on the idea that, in order to accumulate the physiologically active substance specifically in the local region, the remedy should be transported in a high concentration to the local region by using as a carrier a substance which has a high affinity for the morbid part as a wounded site, an inflamed site, and a neoplastic cell proliferation site.

An example of such a carrier is already known in the use of, for example, a cancer-specific antibody as the carrier of an antitumor substance. In this case, the specific accumulation does not take place unless the target cancer has an antigen which is specific to the antibody used as the carrier. Thus, this method has the disadvantage in that its effectiveness is exhibited only in very limited cases. There is no clear example of a carrier being used for an antibiotic. However, a straightforward example of a serious side effect caused by a large-amount administration required for acquiring an effective concentration is seen in the administration of chloramphenicol. Even in this case, it would be possible to avoid the side effect if the main effect can be manifested at a small dose. The same applies to an anti-inflammatory agent as to the antibiotic. Especially for these agents and substances, there exists no specificity like an antigen-antibody reaction in the morbid part, and hence no carrier has been found and no specific accumulation has been tried in the known art.

DETAILED DESCRIPTION OF THE INVENTION

The inventors have found that a fibronectin administered artificially accumulates specifically in morbid parts such as a wounded site, an inflamed site, and a neoplastic cell proliferation site, and hit upon the idea that if the fibronectin is used as a carrier the remedy will be accumulated in the target morbid part irrespective of the presence or absence of a specificity like a specific antibody on the concerned morbid part of the living body. Accordingly, they have prepared various fibronectin-physiologically active substance complex (hereinafter referred to simply as "complex") by combining various physiologically active substances used in the treatment of various diseases with a fibronectin, confirmed their affinity for the morbid part, and thus accomplished this invention.

Thus, this invention relates to a complex which is composed of a fibronectin and a physiologically active substance having a group capable of combining with a protein, and possibly a protein cross-linking agent.

Various names have been given to the fibronectin by the investigators concerned. As can be seen in Shūich Tsukasaki: Tanpakushitsu, Kakusan, Kōso (protein, nucleic acid, and enzyme); Vol. 25, No. 10, 890–905 (1980), it is also designated as cold insoluble globulin, LETS protein, opsonic protein, and cell surface protein. Any of the fibronectins designated as above may be used in this invention. The fibronectin is present, for example, on the cell surface, in the extracellular substrate and in the plasma, and is generally collected and purified from these. Its principal component is dimers, but it contains also monomers. Some of its properties are shown below.

Mobility of main fraction: $\alpha_2$-globulin; molecular weight of main fraction: $4.3$–$4.5 \times 10^5$; isoelectric point: 5.3–6.0; sugar content: about 5%; characteristic as substrate protein: A cross linkage is formed between fibronectins or between a fibronectin and a fibrin-$\alpha$-chain by factor XIII.

The fibronectin used in this invention may contain a small amount of low molecular weight fractions.

The physiologically active substances which can be used in this invention means those which have a promising antitumoral, antibacterial or anti-inflammatory property and which can be combined with a fibronectin by themselves or by the introduction of a group capable of combining with a protein such as an amino or carboxyl group or can react with a fibronectin in the presence of a protein cross-linking agent. Although daunomycin, mitomycin, cephalothin, penicillin G, and secretin will be exemplified in Examples and Test Examples, this invention is not to be limited to these.

The preparation of the "complex" is carried out most preferably by using a known protein cross-linking agent such as glutaraldehyde, carbodiimide, and hexamethylene diisocyanate. Three methods can be used for the preparation, namely a method to mix and react the fibronectin, protein cross-linking agent and physiologically active substance simultaneously, one to react the fibronectin with the protein cross-linking agent followed by reaction with the physiologically active substance, and one to react the physiologically active substance with the protein cross-linking agent followed by reaction with the fibronectin. The reaction is conducted in an aqueous solution of pH 5 to 8, and preferably in a buffer solution. Preferred reaction temperatures are 10° to 30° C., particularly room temperatures. The reaction periods are generally 1 to 24 hours. In any of the above reactions, the molar ratio of the substances to be added may be selected according to the known methods of cross-linking a protein in general. Needless to say, the physiologically active substance is preferably added in excess of the fibronectin.

After completion of the reaction, the "complex" is purified and collected by using an appropriate combination of known methods such as dialysis, gel filtration, salting out, alcohol fractionation, filtration, column chromatography, concentration, and lyophilization.

The present invention will be illustrated more concretely by way of Examples and Test Examples, which do not limit the invention.

In the Examples, the yield of the complex is expressed by the following formula:

$$\text{Yield \%} = \frac{\text{activity of physiologically active substance in the complex}}{\text{activity of starting physiologically active substance}} \times 100$$

EXAMPLE 1

One gram of fibronectin was added to 50 ml of 0.05M sodium phosphate buffer solution, pH 7.4, and the mixture was warmed at 31° C. to 37° C. for about 10 minutes to form a solution. The solution was mixed with 3 ml of 0.1% aqueous glutaraldehyde solution and 15 mg of daunomycin, and stirred gently. The mixture was stirred gently at room temperature for about 6 hours to form a reaction solution. The reaction solution was dialyzed at 15° to 20° C. for about 24 hours against a large amount of water. The dialyzed solution was filtered through a membrane filter (diameter: 0.8 μm) and then subjected to gel filtration at 15° to 20° C. by using a Sephadex G-200 column. The eluted fractions were monitored at 280 nm to collect the effective fractions. The effective fractions obtained were mixed with twice the amount thereof of water, filtered through a membrane filter (diameter: 0.4 μm) and lyophilized to give a fibronectin-daunomycin complex. Yield: 86.5%.

Results of analysis i. Combining ratio of daunomycin with fibronectin[1], 1.2;
ii. Content of low molecular weight fraction (molecular weight of $20 \times 10^4$ or less)[2], less than 5%;
iii. Antigenicity against anti-human fibronectin rabbit serum, positive;

Note:
[1] The combining ratio was calculated from $E_1{}_{cm}^{1\%}$ at λ 495 and $E_1{}_{cm}^{1\%}$ at λ 280 by the use of $\lambda_{max}$: 495 nm and $E_1{}_{cm}^{1\%}$: 206 of daunomycin, and $\lambda_{max}$: 280 nm and $E_1{}_{cm}^{1\%}$: 12.8 of fibronectin.
[2] The content was determined by means of a high-speed liquid chromatography using Waters Protein Column I-250.

EXAMPLE 2

One gram of fibronectin was added to 50 ml of a 0.05M sodium phosphate buffer solution, pH 7.4, and the mixture was warmed at 31° to 37° C. for about 10 minutes to form a solution. The solution was mixed with 5 mg of 1-ethyl-3-(3-dimethylaminopropyl)carbodiimide hydrochloride and stirred at room temperature for about 3 hours. Separately, a 0.04% sodium phosphate buffer solution of mitomycin c was prepared. Twenty ml of the mitomycin c solution was added to the former solution and the mixture was stirred gently at room temperature for 3 hours. The mixture was then dialyzed at 10° to 16° C. for about 24 hours against a large amount of water. The dialyzed solution was filtered through a filter paper and then subjected to gel filtration at 10° to 16° C. by using a Sephadex G-200 column. The eluted fractions were monitored at 280 nm to collect the effective fractions. The effective fractions obtained were filtered through a membrane filter (diameter: 0.45 μm) and then lyophilized to give a fibronectin-mitomycin complex. Yield: 65%.

Results of analysis i. Combining ratio of mitomycin with fibronectin, 1.0;
ii. Content of low molecular weight fraction (molecular weight of $20 \times 10^4$ or less), 5% or less;
iii. Antigenicity against anti-human fibronectin rabbit serum, positive.

EXAMPLE 3

Ten ml of a 0.1% aqueous glutaraldehyde solution was mixed with 1 ml of a 0.1% mitomycin c solution in 0.2M sodium phosphate buffer, and allowed to stand at room temperature for 8 hours. Four ml of the glutaraldehyde-mitomycin reaction solution was added to 50 ml of a separately prepared 2% fibronectin solution in 0.05M sodium phosphate buffer, and the mixture was stirred gently for 5 hours to form a reaction solution. Thereafter, the reaction solution was treated in the same manner as in Example 1 to give a fibronectin-mitomycin complex. Yield: 70.2%.

Results of analysis i. Combining ratio of mitomycin with fibronectin, 1.4;
ii. Content of low molecular weight fraction (molecular weight of $20 \times 10^4$ or less), 5% or less;
iii. Antigenicity against anti-human fibronectin rabbit serum, positive.

EXAMPLE 4

One gram of fibronectin was added to 50 ml of a 0.05M sodium phosphate buffer solution, pH 7.4, and the mixture was warmed at 31° to 37° C. for about 10 minutes to form a solution. This solution was mixed with a solution which had been prepared by dissolving 10 mg of penicillin G potassium in 30 ml of water and regulating the pH of the solution to 5.0 to 6.5 by the use of 1N hydrochloric acid solution and with 10 mg of 1-ethyl-3-(3-dimethylaminopropyl)carbodiimide hydrochloride, and the mixture was stirred gently at room temperature for about 3 hours. The reaction solution was dialyzed at 10° to 15° C. for about 24 hours against a large amount of water. The dialyzed solution was filtered through a membrane filter having a pore diameter of 0.45 μm and then fractionated on a high-speed liquid chromatography using a Toyo Soda SW-3000 column to collect the fractions corresponding to fractionated molecular weight of 200,000 to 600,000. The effective fractions thus obtained were filtered through a membrane filter having a pore diameter of 0.45 μm, and then lyophilized to give a fibronectin-penicillin G complex. Yield: 63%.

Results of analysis i. Combined amount of penicillin G with fibronectin[3], 7.5 mole/mole;
ii. Content of low molecular weight fraction (molecular weight of 200,000 or less), less than 5%;
iii. Antigenicity against anti-human fibronectin rabbit serum, positive.

Note:
[3] The combined amount was calculated based on the amount of penicilline G in the "complex" determined by means of an antigen-antibody reaction using a penicillin G antibody, assuming the averaged molecular weight of the "complex" to be 440,000.

EXAMPLE 5

One gram of fibronectin was added to 50 ml of a 0.05M sodium phosphate buffer solution, pH 7.4, and the mixture was warmed at 31° to 37° C. for about 10 minutes to form a solution. Separately, a solution was prepared by dissolving 40 mg of cephalothin sodium in 10 ml of water and regulating the pH of the solution to 4.0 to 6.0 by the use of 1N hydrochloric acid solution. The cephalothin solution and 40 mg of 1-ethyl-3-(3-dimethylaminopropyl)carbodiimide hydrochloride were added to the fibronectin solution mentioned above, and the mixture was stirred gently at room temperature for about 3 hours. This reaction solution was dialyzed at 10° to 15° C. fo two days and nights against a large amount of water. The dialyzed solution was filtered through a membrane filter having a pore diameter of 0.45 μm, and then fractionated on a high-speed liquid chromatography using a Toyo Soda SW-3000 column to collect the fractions corresponding to fractionated molecular weight of 200,000 to 600,000. The effective fractions thus obtained were filtered through a membrane filter having a pore diameter of 0.45 μm and then lyophilized to give a fibronectin-cephalothin complex. Yield: 25%.

Results of analysis i. Combined amount[4] of cephalothin to fibronectin, 10 mole/mole;
ii. Content of low molecular weight fraction (molecular weight of 200,000 or less)[2], 5% or less,
iii. Antigenicity against anti-human fibronectin rabbit serum, positive.

Note:
[4] The combined amount was calculated based on the amount of cephalothin in the "complex" determined by means of an antigen-antibody reaction using a cephalothin antibody, assuming the averaged molecular weight of the "complex" to be 440,000.

EXAMPLE 6

One gram of fibronectin was added to 50 ml of a 0.05M sodium phosphate buffer solution, pH 7.5, and the mixture was warmed at 20° to 30° C. for about 10 minutes to form a solution. To the fibronectin solution (20 mg/ml), was added 50 mg of a water-soluble carbodiimide, 1-ethyl-3-(3'-dimethylaminopropyl)carbodiimide hydrochloride, the mixture was stirred at 18° C. for 3 hours, and then treated with Centriflow (CF 25, mfd. by Amicon, Inc.) to remove most of the unreacted carbodiimide. Separately, 500 units of secretin was dissolved in 10 ml of the above-mentioned 0.05M phosphate buffer solution. The resulting solution was mixed with the fractions containing the fibronectin-carbodiimide complex in Centriflow mentioned above, and the mixture was allowed to stand at room temperature for about 5 hours with occasional shaking. Thereafter the mixture was fractionated by using SW-3000 column (made by Toyo Soda, Inc.) for high-speed liquid chromatography, to collect the fractions containing the fibronectin-secretin complex eluted at positions corresponding to the molecular weights of 230,000 and 460,000. The amount of fibronectin and of secretin were determined respectively by a method using an antigen-antibody reaction, and the combining ratio of the fibronectin-secretin complex obtained was determined accordingly. The result showed that the combining ratio of the fibronectin-secretin complex obtained by this method was 4000 units of secretin to 1 m mole of fibronectin. Yield: 37%.

Results of analysis i. Conbining ratio of secretin with fibronectin, 4000 units/m mole;
ii. Antigenicity against anti-human fibronectin rabbit serum, positive.

TEST EXAMPLE 1

In order to recognize the accumulation of the administered complex in the tissue and the effect thereof, the procedures in Examples 1, 2, 5, 4 and 6 were repeated respectively except that a $^{125}$I-labelled fibronectin was used and the scale of the experiment was reduced to 1/10 to 1/20, to prepare five labelled complexes with the physiologically active substances indicated in Table 1. The preparation of the $^{125}$I-labelled fibronectin was conducted, by the use of Na$^{125}$I, according to the method of David et al which uses an immobilized lactoperoxidase [Gray S. David: Biochemical and Biophysical Research Communications, 48 (2), 462 (1972)]. Each of the "complexes" had a relative radioactivity of $40 \times 10^4$ cpm/mg or more.

The test animals used were the rats in which a morbid state had been formed. Namely, for cancer-bearing state, a cancer-bearing animal on the 5th day of transplantation was used to which $10^6$ Yoshida sarcoma cells per rat had been transplanted subcutaneously. For a wound state, an animal was used one day after incision, the abdomen of which had been cut with a scalpel and, after application of staphylococcus aureus, sutured lightly. For a gastric ulcer state, an animal was used in which the ulcer had been formed according to the Clamping-Cortisone method [Tadatsuna Tabayashi, Nihon Shōkakibyō Gakkaishi (Japanese Journal of Gastroenterology), 62 (12), 1533 (1965)].

The labelled "complex" was administered to the animal via the tail vein and the animal was killed by poison one day after administration. Then, the injured sites of the animal were collected and the radioactivity was counted by a conventional method. Separately, normal animals receiving no treatment were used as a control. The test results were indicated in terms of the relative ratio of the distributed amount of the labelled "complex", putting that on the abdominal wall of normal tissue as 1.

The results were as shown in Table 1, in which the accumulation in the local region can be clearly recognized.

TABLE 1

| Physilogical-ly active substance | Morbid state of rat used | Accumulation of "complex" Relative ratio (accumulation on abdominal wall = 1) | | | | | Method of sample preparation |
|---|---|---|---|---|---|---|---|
| | | Normal tissue | | | Injured tissue | | |
| | | abdominal Wall | Stomach | Wound | Stomach (ulcer) | Tumor | |
| Daunomycin | (1) | 1 | 2.1 | — | — | 29.4 | 1 |
| Mitomycin | (1) | 1 | 1.9 | — | — | 27.7 | 2 |
| Cephalothin | (2) | 1 | 2.2 | 14.7 | — | — | 5 |
| Penicillin G | (2) | 1 | 1.8 | 15.0 | — | — | 4 |
| Secretin | (3) | 1 | 1.9 | — | 18.9 | — | 6 |

Note:
Animal used: Rat (Groups of five)
Morbid state
(1) Yoshida sarcoma transplanted subcutaneously,
(2) Abdomen incision wound
(3) Tumor caused by Clamping-Cortisone method
Measuring day: 24 hours after administration of labelled "complex"

TEST EXAMPLE 2

The "complexes" prepared in Examples 1, 2, 5 and 6 were administered respectively to rats having the same morbid states as those in Test Exaple 1 to observe their therapeutic effects for morbid states.

Thus, in the cancer-bearing state, the fibronectin-daunomycin complex, fibronectin-mitomycin complex, daunomycin alone, or mitomycin alone was administered through the tail vein, each in a dose of 1.0 mg/kg as daunomycin or 0.30 mg/kg as mitomycin, once a day for consecutive 5 days beginning on the next day to the cancer cell transplantation. The life or death of the animal was observed and the index of life saving (ILS) was determined in a conventional manner.

In the wound state, the fibronectin-cephalothin complex or cephalothin alone was administered through the tail vein, each in a dose of 10 mg/kg as cephalothin, for consecutive 5 days beginning on the day of infliction of the wound to oberve the presence or absence of suppuration on the surface of the wound. In the gastric ulcer state, the fibronectin-secretin complex or secretin alone was administered through the tail vein, each in a does of 0.7 unit/kg as secretin, for consecutive 7 days beginning one day after the ulcer formation, and the animals were killed by poison on the ninth day to observe the presence or absence of erosion, edema and perforation. The results were as shown in Table 2.

TABLE 2

Therapeutic effect

| Physiologically active substance | Effect | | Sample preparation |
|---|---|---|---|
| | Group to which medicine alone was administered | Group to which complex was administered | |
| Daunomycin | ILS 50% | ILS 100% | Example 1 |
| Mitomycin | ILS 47% | ILS 89% | Example 2 |
| Cephalothin | Suppuration was observed in 4 rats. | Suppuration was observed in one rat | Example 5 |
| Secretin | Erosion and edema were observed in 2 rats. Perforation was observed in 3 rats. | Erosion, edema and perforation were observed in one rat. | Example 6 |

TABLE 2-continued

Therapeutic effect

The "complex" of this invention is administered, in a dose corresponding to that of the physiologically active substance contained therein, orally or parenterally, preferably parenterally, and exerts a sufficient therapeutic effect in a smaller dose as compared with the case where the physiologically active substance is administered as it is.

What is claimed is:

1. A method of preparing a fibronectin-drug complex in which fibronectin is connected directly or through a protein cross-linking agent with a drug, the drug being selected from the group consisting of an antitumor agent, an antibacterial and an anti-inflammatory agent, and having a non-peptide group capable of combining with a protein, which method comprises reacting fibronectin, a protein cross-linking agent and said drug having a non-peptide group capable of combining with a protein.

2. A method according to claim 1, wherein the drug is daunomycin, mitomycin, cephalothin, penicillin G or secretin.

3. A method according to claim 1, wherein the protein cross-linking agent is glutaraldehyde, a carbodiimide, or hexamethylene diisocyanate.

4. A method according to claim 1, wherein the reaction is conducted at a temperature of 10° to 30° C.

5. A complex prepared according to the method of claim 1.

6. A method of repairing an injured tissue which comprises administering a complex of claim 5 to an animal having injured tissue.

7. A fibronectin-drug complex in which fibronectin is connected directly or through a protein cross-linking agent with the drug, the drug being selected from the group consisting of an antitumor agent, an antibacterial and an anti-inflammatory agent, which drug has a non-peptide group capable of combining with a protein.

* * * * *